United States Patent [19]
Bowen et al.

[11] Patent Number: 5,356,641
[45] Date of Patent: Oct. 18, 1994

[54] PROCESS FOR PREPARING AN OAK WOOD EXTRACT AND DISTILLATE

[75] Inventors: David Bowen, Baltimore; Jan Benning, Cockeysville; Chris Bronzert, Owings Mills; Alan Ellison, Hampstead, all of Md.

[73] Assignee: Indopco, Inc., d/b/a Quest International Flavors & Food Ingredients Company, Owings Mills, Md.

[21] Appl. No.: 58,706

[22] Filed: May 10, 1993

[51] Int. Cl.$^5$ .................. A23L 1/0534; A23L 1/22
[52] U.S. Cl. .................. 426/52; 426/429; 426/492; 426/493; 426/650; 426/655
[58] Field of Search .......... 426/51, 655, 49, 52, 426/650, 592, 429, 492, 493; 424/195.1

[56] References Cited

U.S. PATENT DOCUMENTS 2,347,783  10/1941  Krebs ........................ 426/49

FOREIGN PATENT DOCUMENTS 2356722  1/1978  France .
7018980  1/1982  Japan .
9011159  1/1984  Japan .

OTHER PUBLICATIONS

Sadovodstvo, Vinogradarstvo i Vinodelie Moldavii, 25(12):26–29, 1970.
Vinodelie i Vinogradarstvo, 29(7):13–16, 1969.
Australian & New Zealand Wine Industry Journal, 6(1):69–72, 1991.
Journal of the Association of Official Analytical Chemists, 73(4):498–501, 1990, Abstract.
Connaissance de la Wigne et du Via, 21(3):169–190, 1987, Abstract.
American Journal of Enology and Viticulture, 36(2):148–155, 1985, Abstract.
American Journal of Enology and Viticulture, 34(4):211–215, 1983, Abstract.
Wines and Vines, 60(1):40–43, 1979, Abstract.
Bulletin de l'Office International du Vin, 44(482):339–355, 1971, Abstract.
Vinodelie i Vinogradarstvo SSSR, 31(2):3–31, 1971, Abstract.
Soviet Patent Abstract of SU 1033539, Aug. 1983 from Derwents WPI file Acc. #84–119222/19.
Soviet Patent Abstract of SU 962295, Sep. 1982 from Derwents WPI file Acc. #83–739163/33.
Soviet Patent Abstract of SU 753896, Aug. 1980 from Derwents WPI file Acc. #818–28529D/16.
Soviet Patent Abstract of SU 734269, May 1980 from Derwents WPI file Acc. #81–05143D/04.
Soviet Patent Abstract of SU 247892 from Derwents WPI file Acc. #70–29150R/17.
French Patent Abstract of FR 2356722, Mar. 1978 from Derwents WPI file Acc. #78–25811A/14.
German Patent Abstract of DD 212051, Aug. 1984 from Derwents WPI file Acc. #87–094263/14.
Soviet Patent Abstract of SU 1414866, Aug. 1988 from Derwents WPI file Acc. #89–149024/20.
Soviet Patent Abstract of SU 1421767, Sep. 1988 from Derwents WPI file Acc. #89–083555/11.
Soviet Patent Abstract of SU 1291601, Feb. 1987 from Derwents WPI file Acc. #87–312546/44.
Soviet Patent Abstract of SU 1198115, Dec. 1985 from Derwents WPI file Acc. #86–182149/28.

*Primary Examiner*—Donald E. Czaja
*Assistant Examiner*—Curtis E. Sherrer
*Attorney, Agent, or Firm*—Cushman, Darby & Cushman

[57] ABSTRACT

A process for obtaining a blending and ageing additive from oak wood which comprises (a) mixing oak wood in subdivided or particulate form with water, alcohol or mixture thereof; (b) enzymatically digesting the mixture at elevated temperature; (c) adding wine or other alcohol to the digestion mixture after the digestion is completed; (d) refluxing the resulting mixture at elevated temperature until the wood changes color and the liquid phase no longer changes color; (e) separating the resulting liquid phase from the wood; and (f) distilling the liquid phase to obtain a clear or water-white distillate and solid extract. The distillate and/or extract may be added to wine or other beverage, or other composition such as vinegar, to improve properties thereof.

5 Claims, No Drawings

PROCESS FOR PREPARING AN OAK WOOD EXTRACT AND DISTILLATE

The present invention is concerned with blending agents derived from oak wood and the use of such agents for blending with alcoholic and non-alcoholic beverages such as wines or spirits or vinegar, sauces, dressings or the like.

Oak wood and extracts thereof have an extensive history in the flavoring and/or ageing of wines. For example, U.S. Pat. No. 5,102,675 describes the use of toasted oak for use in ageing wine. The oak, in divided form, is soaked in water or ethanol to remove undesirable soluble flavors and the oak is toasted. The toasted oak is then added to the wine and the wine is aged.

SU 1414866-A describes ageing blends of spirits distilled from wine and oak extracts. U.S. Pat. No. 4,350,708 discloses the preparation of oak flavors for ageing alcoholic beverages. Oak pieces are first extracted with alcohol and then extracted with demineralized water. The product is used for ageing wines, alcohols and other liquors. French 2,356,722-A also describes the production of an oak extract for use in ageing spirits, e.g. brandy. The extract is obtained by extracting finely divided oak with alcohol solutions. SU 1421767-A and SU 1291601-A also describe the addition of oak extracts to wines or alcoholic beverages. See also DD-212051-A,B and SU 1198115-A which disclose the addition of oak extracts to wines prior to ageing.

Other disclosures relating to the addition of oak wood extracts to wine or other beverages to facilitate ageing and/or improve taste include: SU 1033539-A; SU 962295-A; and U.S. Pat. No. 4,463,024.

SU 247892-A discloses the use of an oak wood extract with alcoholic beverage to shorten the maturing time and improve quality. The extract is prepared by treating the oak wood with chemicals and heating after which the extract is passed through an anionic and cationic de-ionizer and then vacuum concentrated and dried.

A study of the effect of various wood extracts to accelerate maturation of brandies, whiskey and other strongly alcoholic drinks, is described in *Sadovodstvo, Vinogradarstvo i Vinodelie Moldavii,* 25(12): 26–29, 1970. Extracts were obtained by treating oak wood with HCL, ammonia and heat with subsequent extraction. The results showed that the most effective results were obtained with an alcohol-water fraction with the basic tannins and in hydrocarbons with added aromatic aldehydes.

A further paper in *Vinodelie i Vinogradarstvo,* 29(7): 13–16, 1969 describes the changes in carbohydrates of oak fibers in ethanol mediums and the migration of sugars from such fibers into brandy.

It is also known to store or age wine or other alcoholic beverages in the presence of oak wood. See, for example, SU 753896-B; SU 734269-B; *Australian & New Zealand Wine Industry Journal,* 6(1): 69–72, 1991; *Journal of the Association of Official Analytical Chemists,* 73(4): 498–501, 1990; *Connaissance de la Wigne et du Via,* 21(3): 169–190, 1987; *American Journal of Enology and Viticulture,* 36(2): 148–155, 1985; *American Journal of Enology and Viticulture,* 34(4):211–215, 1983; *Wines and Vines,* 60(1): 40–43, 1979; *Bulletin de l'Office International du Vin,* 44(482): 339–355, 1971; *Vinodelie i Vinogradarstvo SSSR,* 31(2): 30–31, 1971.

It will be evident from the foregoing that extensive efforts have gone into the use of oak wood and various extracts thereof for the purpose of improving the ageing and/or taste of alcoholic beverages including wines and for understanding the reasons for any such improvements. However, notwithstanding such efforts, there still remains considerable room for improving the rate of ageing and taste of wine and alcoholic beverages. There is also considerable interest in providing improved blending agents for use with non-alcoholic beverages as well as with flavoring agents such as vinegar, sauces and the like.

SUMMARY OF THE INVENTION

The purpose of the present invention is to provide certain improvements in oak wood extracts for use with wine and other alcoholic and non-alcoholic beverages as well as with such flavoring materials as vinegar and sauces. These extracts have been found to have a number of advantages including, for example, the shortening of the ageing time for wines and improvement in taste. Other advantages include, for example, the provision of a more complex character to wine and the ability to standardize organoleptic properties and batch-to-batch variations.

An important aspect of the invention is the provision of a process which includes enzymatic digestion and distillation of oak wood in admixture with wine or other alcohol.

Another feature of the invention is the use of the distillate obtained by the present process, or concentrate thereof, as an additive to wine, or the equivalent, advantageously mixed with a dark residue obtained by the present process, to improve taste and ageing characteristics.

Other features of the invention will be evident from the more detailed description of the invention which follows.

DETAILED DESCRIPTION OF THE INVENTION

The present process for obtaining a blending or ageing additive from oak wood comprises (a) mixing oak wood in subdivided or particulate form with water or aqueous alcoholic liquid containing up to, for example, 50% by weight of alcohol, e.g. wine or spirit; (b) enzymatically digesting the mixture at elevated temperature; (c) adding wine or other alcohol to the digestion mixture after the digestion is completed; (d) refluxing the resulting mixture at elevated temperature until the wood changes color and the liquid phase no longer changes color; (e) separating the resulting liquid phase from the wood; and (f) distilling the liquid phase to obtain a clear or water-white distillate and a dark syrup-like residue (hereinafter called the "solid extract"). Both the distillate, and solid extract are suitable for addition to wine or other beverage to improve the flavor thereof. Preferably the distillate and solid extract are used together although either component, can be used alone. Significantly equivalent results are not obtained if the distillation step (f) is omitted. The reason for this is not understood but apparently the distillation or refluxing step tends to generate flavors thus improving the results obtained.

Preferably the initial mixing (a) of the wood and alcohol, which is advantageously wine but not necessarily so, is carried out at ambient temperature although other temperatures may be used. However, the enzymatic digestion (b) is desirably conducted at an elevated temperature where the enzymes involved are most active, usually 50°-60° C., although lower and higher temperatures can also be used. The digestion will normally take from 4-8 hours. The course of the digestion is evident as the mixture turns into a smooth slurry with a brownish gray striation as the digestion proceeds.

If the mixture becomes too viscous as the digestion proceeds, more wine or other alcohol can be added to give a viscosity suitable for mixing during digestion. After the digestion, the digested mixture is preferably allowed to cool to room temperature. Preferably the same kind of wine or alcohol is added to the digested mixture in step (c) as is used to form the initial mixture for digestion in (a). The amount of wine or the like added at this post-digestion stage can be varied but usually will be in the order of 50-200% by weight of the wine or other alcohol used in the beginning.

Refluxing (d) of the mixture at, for example, 75°-100° C., is conducted in a closed vessel for from about 4-10 hours. The wood changes color during this refluxing and becomes progressively lighter. The refluxing can be discontinued with the color of the liquid present becomes dark and does not change significantly on further heating. At this stage, the colored liquid phase is separated from the wood, preferably by decanting or filtering in step (e) to give what is conveniently called a "pre-concentrate" liquid phase and the wood phase.

The pre-concentrate is then distilled, preferably under vacuum, in step (f) at a temperature of, for example, 50° to 100° C., preferably about 80-85° C., to give a water-white distillate, leaving a colored residual liquid in the distillation vessel. This colored liquid is further distilled, preferably in a roto-evaporator, to give more water-white distillate which can be mixed with the distillate earlier obtained for use in ageing and flavoring wine or other beverages. This distillation step leaves a solid extract or residue which is desirably used with the clear white distillate for purposes of the invention. This solid extract is, generally speaking, a sludge-like mass with a brix value of, for example, 60-90. This is soluble in wine or alcohol and, as noted is desirably used with the distillate for blending according to the invention.

The alcohol content of the distillate obtained in (f) can be varied but usually will be in the range of 8-15% by weight. This distillate may be used directly as an additive to wine or the like, with or without the solid extract. Alternatively, the distillate may be even further concentrated by distillation, for example, by column or reverse phase chromatography or vacuum distillation, to give a further concentrate which is also suitable for use, as such or mixed with solid extract, as a blending or ageing additive to wine or the equivalent.

Any available oak wood may be used for present purposes. Typically available oak woods include American White Oak; American medium toast oak chips; Medium toast French oak and dark toast French oak. These or other types of oak wood are used in subdivided or particulate form, e.g. as chips, dust or the equivalent. It may also be possible to use other types of wood, e.g. beechwood, as a replacement for oak wood. This depends on the nature of the liquid to be blended with the blending additive of the invention. For example, beechwood may be a useful replacement for oak wood when the additive is to be used with vinegar or beer.

Advantageously, wine is used as the alcohol component in the various steps of the process. However, for example, aqueous alcoholic solutions, e.g. ethanolic solutions or other types of alcohol solutions may also be used.

The enzymatic digestion may be carried out using any available type of biocellulase enzyme. Typical examples include BIOCELLULASE A20 and BIOCELLULASE TRI (Quest Bioproducts). Other enzymes consistent with the purpose of the invention can also be used.

The invention can be used for improving the ageing and taste characteristics of any type of wine or alcoholic beverage. The invention is illustrated herein utilizing a Chablis Blanc type wine. However, other white or red wines may be used in the practice of the invention. Additionally, other alcoholic beverages, e.g. whiskeys, brandies, cognacs and the like may also be used. Vinegar may also be. Non-alcoholic beverages or flavors, e.g. sauces, may be similarly modified using the distillate described herein as such or in admixture with the solid extract.

The invention is illustrated, but not limited, by the following example:

EXAMPLE 412.50 grams of wine (Chablis Blanc with 11% alcohol content) at room temperature (about 25° C.) was placed in a glass flask. Thereafter, 82.50 grams of oak wood chips were gradually added to the wine with slow mixing. Mixing speed was escalated as the amount of wood in the wine increased. Care was taken to position the mixing blade so that all of the material was kept moving.

Heat was then applied to the mixture to bring the temperature of the mixture to 60° C. The vessel was kept covered as well as possible to minimize alcohol evaporation.

5 grams of biocellulase (BIOCELLULASE A20) were then carefully added to the mixture of wood and wine. Mixing was continued with the temperature maintained at between 50-60° C. to maximize enzyme effectiveness. The vessel was maintained covered throughout and digestion at 50-60° C. was allowed for 8 hours. The mixture turned into a smooth slurry and a brownish-gray striation appeared after about 4 hours of digestion.

At the end of the digestion, when the enzyme has decreased in activity due to the acidic media and the presence of 11% alcohol, the reaction batch was allowed to cool to room temperature with mixing.

500 grams of the same wine were then added to the digested mixture with mixing. Once the mixture reached homogeneity, the batch was transferred to a closed flask provided with a condenser column.

The mixture was allowed to percolate with reflux at 80° C. for 8 hours while mixing. As the heating proceeded, the wine present became a progressively darker shade of amber-brown. The wood began to take on a lighter tan color as opposed to its original light-brown color. After 8 hours of heating at 80° C., the heating was discontinued and the flask allowed to cool to room temperature with mixing.

The liquid (pre-concentrate) phase of the batch was then separated from the wood residue. This was done by decanting the amber liquid from the mass and filtering the liquid thus collected through filter paper at ambient or room temperature. The yield of liquid was about 700 grams (from a 1,000 gram batch). The thus separated liquid was kept sealed and under refrigeration to avoid possible oxidative deterioration or microbiological contamination. Enzyme activity was shown analytically to be non-existent after the reflux heating step was completed.

The filtered liquid, conveniently termed the "pre-concentrate", was then transferred to a distillation unit. Vacuum was applied as the temperature was raised to 80° C. in a mantle-held flask. A stand pipe was used in the holding flask as a means of minimizing the risk of pulling over the colored residual liquid into the water-white clear fraction that was distilled off and collected. The heating to 80° C. was gradual and an equilibrium was achieved which resulted in a 20 in. Hg vacuum with the contents of the holding flask at 75° C. Approximately 1 kilogram of clear white distillate was obtained per hour.

After about 90% of the original liquid mixture (pre-concentrate) had distilled over as the indicated clear distillate or concentrate, the remaining pre-concentrate was placed into a roto-evaporator and concentrated to 78 brix. The clear distillate from this step and the initial distillate from the pre-concentrate were then combined to provide the final blending product as a clear water-white liquid distillate. The alcohol content of this product was about 10.80% by weight. It was added, in the amount of about 2% by weight, to Chablis Blanc type wine which was then conventionally aged for about 4 days. The aged product had an excellent taste characterized by a smooth well-rounded body typical of wines which had been aged for longer periods of time. When compared with conventionally prepared "oaked" wine, i.e. wine aged for several weeks in the presence of added oak chips, and blends thereof with non-oaked wine, wine blended with the distillate of the invention, demonstrated better body and flavor characteristics among other desirable properties.

It will be recognized that various modifications may be made in the invention exemplified above and as otherwise described herein. For example, in the foregoing example, the clear white distillate of the invention may be usefully added in amounts ranging from about 0.1–10% by weight, or even more or less, to the same or different wine. Additionally the wine, with distillate added, may be aged for other periods of time, e.g. 3–7 days or even more. An amount of the solid extract (e.g. 0.5–5% by weight) may also be usefully mixed with the distillate for addition to wine or the equivalent to obtain the advantages of the invention. Other variations will also be evident to those in the art. Accordingly, the scope of the invention is set out in the following claims wherein:

We claim:

1. A process for obtaining a distillate and an extract comprises:
   (a) mixing oak wood in subdivided or particulate form with water, alcohol or mixture thereof;
   (b) enzymatically digesting the mixture obtained in (a) at elevated temperature;
   (c) adding wine or alcohol to the digestion mixture after the digestion is completed;
   (d) refluxing the resulting mixture at elevated temperature until the liquid phase becomes dark and no longer changes color;
   (e) separating the resulting liquid phase from the wood; and
   (f) distilling the liquid phase to obtain a clear or water-white distillate and a dark syrup-like extract both of which are suitable for addition to wine or other alcoholic beverages, vinegar, non-alcoholic beverages or sauces to improve the flavor or organoleptic properties thereof.

2. The process of claim 1 wherein the enzymatic digestion is carried out using a cellulase enzyme.

3. The process of claim 2 wherein the enzymatic digestion is carried out at 50°–60° C.

4. The process of claim 1 wherein wine is mixed with the oak wood in step (a) and wine is used in step (c).

5. The process of claim 1 wherein the distillate in (f) is further concentrated before use.

* * * * *